United States Patent [19]

van der Jagt

[11] Patent Number: Plant 6,467

[45] Date of Patent: Dec. 13, 1988

[54] CHRYSANTHEMUM NAMED RENDU GOLD

[75] Inventor: Martinus van der Jagt, Ter Aar, Netherlands

[73] Assignee: Chrysanthemum Breeders Association, N.V., Curacao, Netherlands Antilles

[21] Appl. No.: 3,543

[22] Filed: Jan. 15, 1987

[51] Int. Cl.[4] ..... A01H 5/00

[52] U.S. Cl. ..... Plt./78

*Primary Examiner*—Robert E. Bagwill
*Attorney, Agent, or Firm*—Parkhurst & Oliff

[57] ABSTRACT

A new and distinct cultivar of Chrysanthemum plant named Rendu Gold, bearing medium sized red/yellow blooms with a red center and a performance of fourteen days.

3 Drawing Sheets

BACKGROUND OF THE NEW PLANT

The new plant of the present invention relates to the Chrysanthemum genus.

ORIGIN AND HISTORY OF THE NEW PLANT

The new plant according to the present invention comprises a new and distinct cultivar of chrysanthemum plant which is color mutant of a Chrysanthemum named Rendez Vous. The new cultivar was discovered by Martinus van der Jagt at Paradijsweg 88, Ter Aar, Holland. The new cultivar has been asexually reproduced by cuttings at the same location, and has been found to retain its distinctive characteristics through successive propagations.

SUMMARY OF THE NEW PLANT

The present invention is a new and distinct variety of Chrysanthemum of a medium sized bloom and red/yellow color.

BRIEF DESCRIPTION OF THE DRAWINGS

The present new and distinct Chrysanthemum cultivar is shown in the accompanying drawings, the color being as nearly true as possible with color photographs of this type.

Sheet 1 shows the full bloom of the new cultivar;

Sheet 2 shows various stages of bloom of the new cultivar; and

Sheet 3 shows the foliage of the new cultivar.

DESCRIPTION OF THE NEW PLANT

This new variety of chrysanthemum is of the botanical classification *Chrysanthemum morifolium,* named Rendu Gold. When grown in the vicinity of Ter Aar, Holland, it has a response time of approximately eight (8) weeks. This new variety produces medium sized yellow blooms with a red center and having a performance of fourteen days. This new variety of chrysanthemum has been found to retain its distinctive characteristics throughout successive propagations and may be planted under conventional greenhouse conditions in Holland between weeks fifty-thirty six (50-36).

The following is a description of the plant and characteristics that distinguish it over related known varieties and its antecedents:

Botanical classification: *Chrysanthemum morifolium.*

Bud:

*Size.*—Large (cross section: 1.5 cm height: 1.5 cm).
*Form.*—Round and flat.
*Outside color.*—Orange red 31 A.

Bloom:

*Size.*—Medium.
*Fully expanded.* 6.5-7 cm.
*Borne.*—Several.
*Stems.*—Strong.
*Form.*—Decorative.
*Permanence.*—Appr. 14 days (at 18°-20° C.).

Color:

*Center of flower (Disk Floret).*—Orange red 34 A.
*Base of petals.*—Orange red 34 A.
*Inside of petals.*—Orange 25 B.
*Reverse of petals.*—Orange 25 B.
*Outer petals.*—Yellow orange 21 A.
*Tonality from a distance.*—A yellow decorative with a red center.
*Discoloration.*—May discolor to yellow orange 21 C at maturity.

Petals:

*Texture.*—Upperside: Smooth. Underside: Smooth.
*Number.* 13 (Excluding red center part) approx. 85-95.
*Cross-section.*—Inner petals:convex. Outer petals:-concave.
*Arrangement.*—Imbricated.
*Persistence.*—Normal.
*Fragrance.*—Typical Chrysanthemum.

Reproductive organs:

*Stamens.*—Some in the petals. Length: 3 mm.
*Pollen.*—None.
*Styles.*—Some, yellow, thin Length: 3 mm.
*Stigmas.*—Yellow, width approx. 0.5 mm.
*Ovaries.*—Enclosed in calyx.

Plant:

*Form.*—Spray mum meant for erect culture. Herbaceous.
*Growth.*—Medium to vigorous.
*Height.*—95-100 cm.
*Peduncle.*—Near the top: 12 cm. Near the middle: 15 cm. Near the bottom: 20 cm.
*Internodes.*—2.5-3 cm.
*Flowering Response.*—Eight weeks.

Foliage:

*Color.*—Upperside: Green 136 A. Underside: Greyed green 189 A.
*Size.*—Large. Length: 14 cm. Width: 10.5 cm.
*Quantity.*—35.

*Shape.*—Oval, undulated.

*Texture.*—Uppperside: Smooth. Underside: Smooth.

*Ribs and Veins.*—Ribs normally developed; veins not so well developed. Upperside: Ribs clearly marked, veins normally marked. Underside: Ribs clearly marked, veins not marked.

*Edge.*—Some crenation.

In the description above, color references are made to the "R.H.S. Colour Chart" issued by The Royal Horticultural Society, in association with The Flower Council of Holland, Edition February 1986.

What is claimed:

1. A new and distinct cultivar of Chrysanthemum named Rendu Gold, as described and illustrated in the foregoing specification and accompanying drawings.

* * * * *

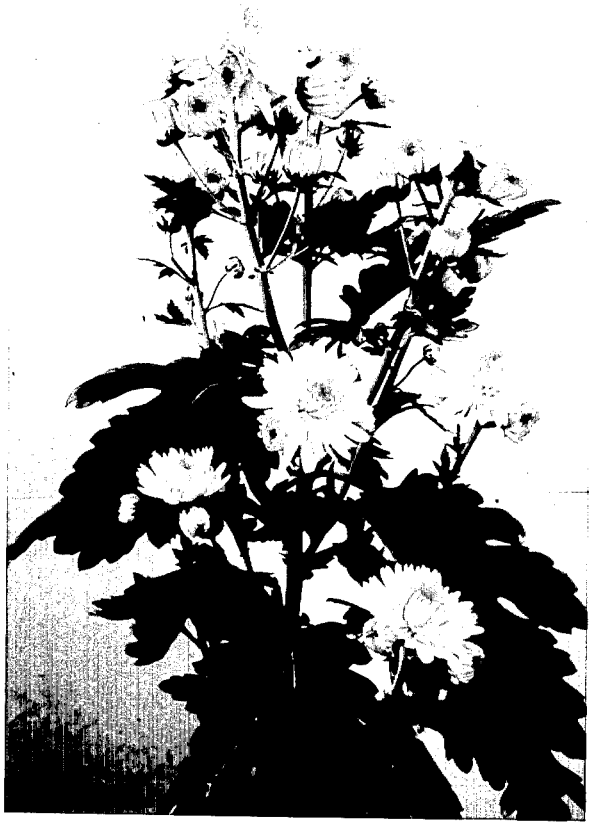

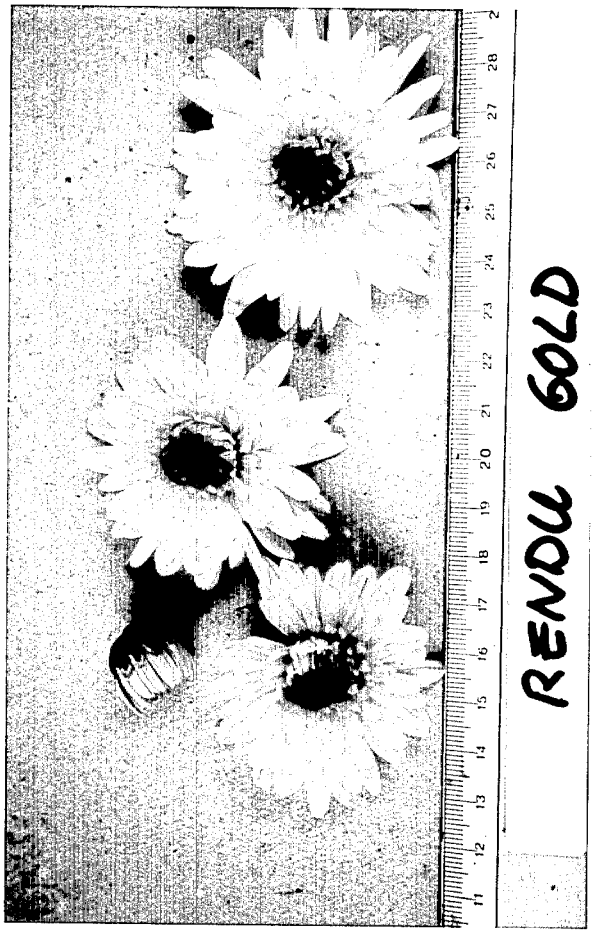
RENDU GOLD

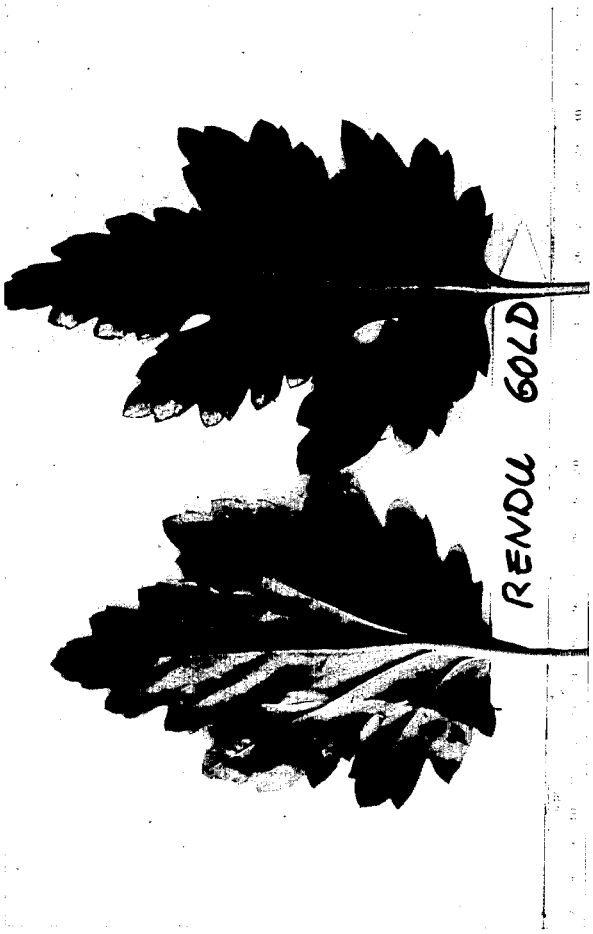
RENDU GOLD